US00PP33599P2

(12) United States Plant Patent
Ault

(10) Patent No.: US PP33,599 P2
(45) Date of Patent: Nov. 2, 2021

(54) ***TEUCRIUM* PLANT NAMED 'PRIDE OF GEORGIA'**

(50) Latin Name: ***Teucrium chamaedrys* subsp. *nuchense***
Varietal Denomination: Pride of Georgia

(71) Applicant: James Robert Ault, Libertyville, IL (US)

(72) Inventor: James Robert Ault, Libertyville, IL (US)

(73) Assignee: CHICAGOLAND GROWS, INC., Glencoe, IL (US)

( * ) Notice: Subject to any disclaimer, the term of this patent is extended or adjusted under 35 U.S.C. 154(b) by 0 days.

(21) Appl. No.: 17/130,629

(22) Filed: Dec. 22, 2020

(51) Int. Cl.
*A01H 6/00* (2018.01)
*A01H 5/02* (2018.01)

(52) U.S. Cl.
USPC ..... Plt./263.1

(58) Field of Classification Search
USPC ..... Plt./263.1
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Teucrium* plant named 'Pride of Georgia' that is characterized by its rhizomatous spreading herbaceous perennial habit in contrast to most wall germanders (*T. chamaedrys*) being clumping subshrubs with a woody base, its blooms that are present for 7 to 9 weeks, its low growing compact plant habit, and its vigorous spreading plant habit.

2 Drawing Sheets

Botanical classification: *Teucrium chamaedrys* subsp. *nuchense*.

Variety denomination: 'Pride of Georgia'.

BACKGROUND OF THE INVENTION

The present invention relates to a new and distinct cultivar of *Teucrium chamaedrys* subsp. *nuchense* and will be referred to hereafter by its cultivar name, 'Pride of Georgia'. 'Pride of Georgia' is a new cultivar of wall germander; an herbaceous perennial plant grown for landscape use.

The new cultivar was selected as a seedling in a trial field by the Inventor in Glencoe, Ill. The trial field was originally planted with seeds of unnamed and unpatented plants of *Teucrium chamaedrys* subsp. *nuchense* in 2011. Seedlings derived from open pollination of plants from the original planted seeds were evaluated. The exact parentage is unknown. 'Pride of Georgia' was selected as a single unique plant from the trials in July of 2014 for its compact plant habit and short upright inflorescences.

Asexual propagation of the new cultivar was first accomplished by shoot tip cuttings by the Inventor in August of 2014 in Glencoe, Ill. Asexual propagation by shoot tip cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Pride of Georgia' as a unique cultivar of *Teucrium*.

1. 'Pride of Georgia' exhibits a rhizomatous spreading herbaceous perennial habit in contrast to most wall germanders (*T. chamaedrys*) being clumping subshrubs with a woody base.

2. 'Pride of Georgia' exhibits blooms for 7 to 9 weeks.
3. 'Pride of Georgia' exhibits a floriferous blooming habit with blooms covering 100% of the plant for at least three weeks of the bloom period.
4. 'Pride of Georgia' exhibits a low growing compact plant habit.
5. 'Pride of Georgia' exhibits a vigorous spreading plant habit.

The possible female parents of 'Pride of Georgia' all differ from 'Pride of Georgia' in having taller plant heights with unreliable cold hardiness in U.S.D.A. Zone 5. 'Pride of Georgia' can be compared to the *Teucrium chamaedrys* cultivars 'Nana' (not patented) and 'Prostratum' (not patented). 'Nana' and 'Prostratum' are both similar to 'Pride of Georgia' in having a lower growing habit than standard wall germanders and in being reliably cold hardy to U.S.D.A. Zone 5. 'Nana' differs from 'Pride of Georgia' in having a much taller plant height, less bloom coverage, and a clump-forming plant habit, barely spreading at the end of its third year in-ground. 'Prostratum' differs from 'Pride of Georgia' in having a taller plant height, densely pubescent stems that make the stem surface appearance white in color, and foliage that is darker green in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to a website listing by Chicago Botanic Garden.

BRIEF DESCRIPTION OF THE DRAWINGS

The accompanying color photographs illustrate the overall appearance and distinct characteristics of a 4-year-old plant of the new *Teucrium* as grown in a trial garden in Glencoe, Ill.

The photograph in FIG. 1 provides a view of the spreading plant habit of 'Pride of Georgia' in bloom.

Figure 1:
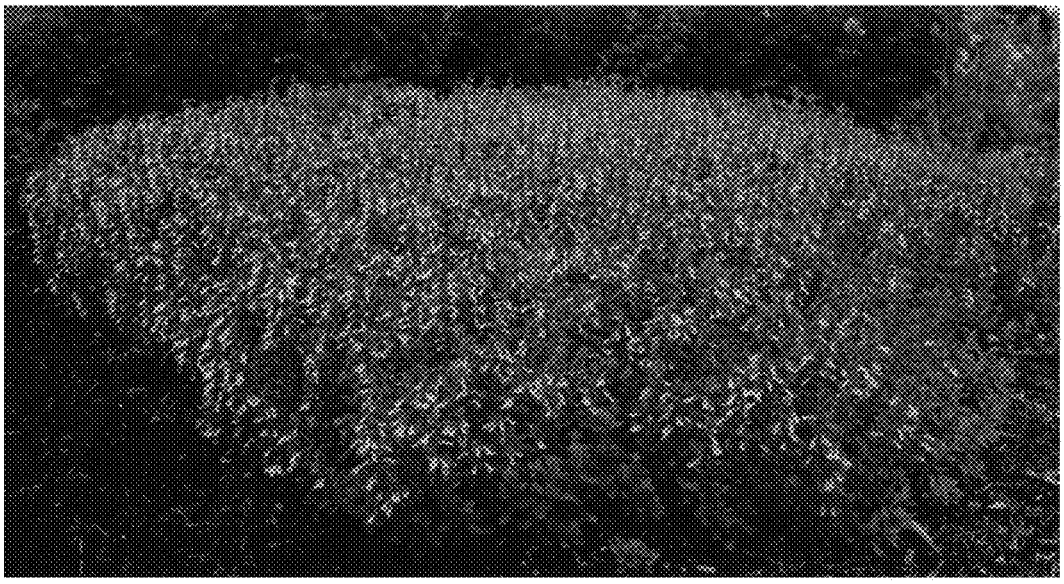
Figure 2:
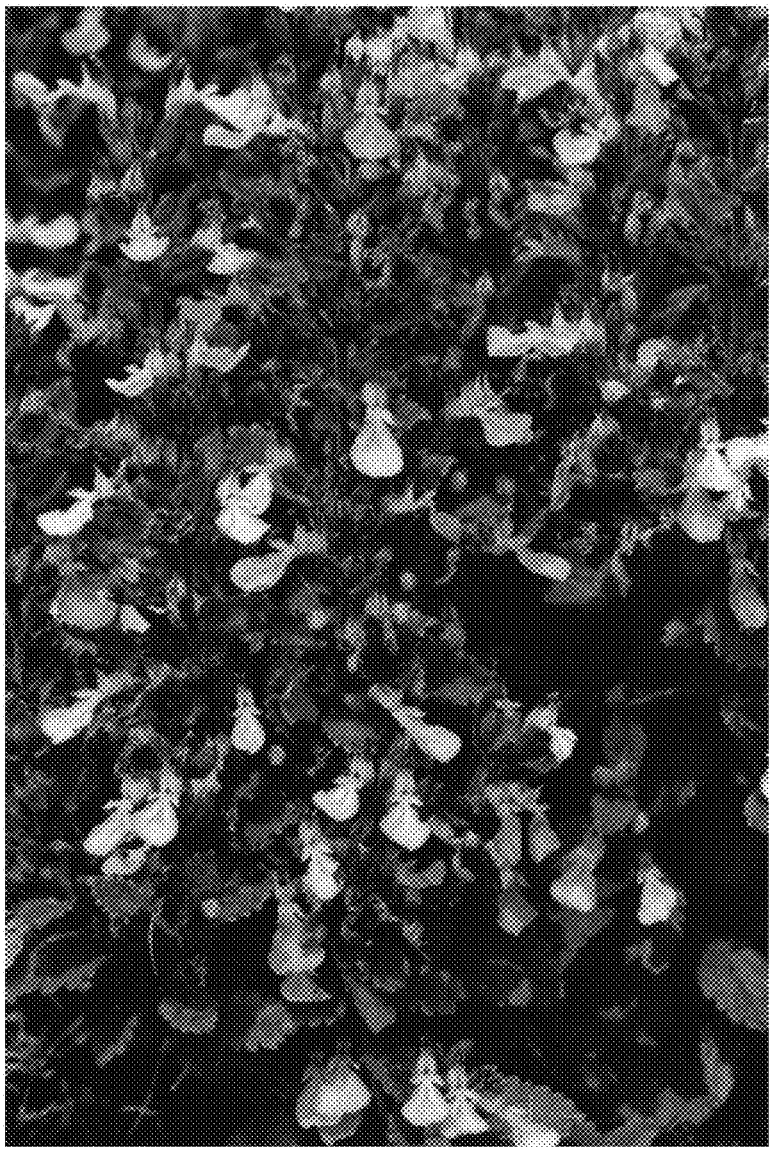

The photograph in FIG. 2 provides a close-up view of the inflorescences of 'Pride of Georgia'.

The colors in the photographs may differ slightly from the color values cited in the detailed botanical description, which accurately describe the colors of the new *Teucrium.*

DETAILED BOTANICAL DESCRIPTION

The following is a detailed description of the new cultivar taken both from plants 24 months in age as grown outdoors over summer in one-quart containers and from one to three-year-old trial plants grown in-ground in Glencoe, Ill. The color determination is in accordance with The 2015 Colour Chart of The Royal Horticultural Society, London, England, except where general color terms of ordinary dictionary significance are used.

General description:

*Blooming period.*—Average of seven weeks commencing in early to mid-July and finishing in early to mid-September in U.S.D.A. Zone 5, the red-purple calyces can persist into early October.

*Plant type.*—Herbaceous perennial.

*Plant habit.*—Rhizomatous and spreading.

*Plant size.*—1-year-old plants; 12 cm in height, 45 cm in spread, 3-year-old plants; 12 cm in height, 112 cm in spread.

*Hardiness.*—At least in U.S.D.A. Zones 5 to 8.

*Diseases and pests.*—No susceptibility or resistance to diseases or pests has been observed.

*Root description.*—Fibrous and fine, N155D in color.

*Root development.*—Time required for root initiation is 3 weeks if cuttings are taken in early June, time required to produce a young plant from rooted cutting is 4 months from a rooted cutting to fill a SVD4 pot with plants bloom the following year.

*Propagation.*—Stem tip cuttings.

*Growth rate.*—Vigorous.

Stem description:

*Shape.*—Rounded.

*Stem color.*—Young stems; 145B, randomly flushed with 186A as the stems mature, mature stems; 187A and N186A.

*Stem size.*—An average of 11 cm in length and 2 mm in diameter.

*Stem surface.*—Young and mature stems; densely covered with very short soft hairs; an average of 0.5 mm in length with color matching stem surface.

*Stem aspect.*—Upright to slightly outward.

*Internode length.*—Up to 1.5 cm in length.

*Branching.*—Average of 30 basal branches growing from base.

*Stem strength.*—Strong to moderately strong.

Foliage description:

*Leaf shape.*—Ovate.

*Leaf division.*—Simple.

*Leaf base.*—Acute.

*Leaf apex.*—Acute to obtuse.

*Leaf venation.*—Pinnate, upper and lower surface color; translucent and 145D in color.

*Leaf margins.*—Serrate.

*Leaf arrangement.*—Opposite and whorled.

*Leaf attachment.*—Sessile.

*Leaf surface.*—Upper surface; very slightly glossy, soft, pilose, densely covered with short and soft hairs, 0.5 mm in length, matching surface color, lower surface; matte and puberulent, moderately covered with very minute hairs too small to measure size or color.

*Leaf size.*—Up to 2 cm in length and 1.2 cm in width.

*Leaf quantity.*—Average of 50 per stem 11 cm in length.

*Leaf color.*—Upper surface 144A, lower surface N148D.

*Leaf fragrance.*—None.

Inflorescence description:

*Inflorescence type.*—Terminal raceme of labiate flowers.

*Lastingness of inflorescence.*—Individual flowers average of 5 days, self cleaning.

*Inflorescence size.*—An average of 4 cm in length and 5 cm in diameter.

*Flower type.*—Labiate.

*Flower aspect.*—Held in multiple angles, whorled.

*Flower number.*—Average of 14 per inflorescence.

*Flower fragrance.*—Moderate and pleasant.

*Flower buds.*—Oblanceolate in shape, 6 mm in length, 3 mm in diameter, young buds 145A and 145C in color, as they maturing to a blend of N186A and 187A, base 145C, densely covered with pubescence up to 0.7 mm in length and NN155C in color.

*Flower size.*—Average of 2.5 cm in length and 1.5 cm in width.

*Peduncle.*—An average of 4 mm in length and 1 mm in diameter, color; 143B, moderately strong in strength, surface is densely covered in pubescence; average of 0.4 mm in length and the same as the stem color.

*Pedicel.*—None, flowers are sessile to peduncle.

*Calyx.*—Rotate and campanulate in shape, average of 1 cm in length and 3 mm in diameter.

*Sepals.*—5, rotate, base is fused 80%, lanceolate in shape, entire margins, 20% of apex is free and narrow acute and 3 mm in length, entire margins, outer surface is slightly glossy and densely pubescent hairs up to 0.3 mm in length and match surface color, inner surface is very glossy and glabrous, color; outer surface 147A, inner surface 143C, color of both surfaces turn 177A as the flowers mature.

*Petals.*—Labiate, lower lip; 3-lobed, cup-shaped and obcordate in shape, lobed margins and slightly undulate, apex obtuse and notched up to 2 mm in depth, 1.5 cm in length and 9 mm in width, based fused, upper and lower surface smooth, slightly glossy, sheen and glabrous, lower surface along the center is densely covered in pubescence up to 2 mm in length and NN155A in color, color; young upper and lower surface 76C and 76D, margins faintly flushed with 76A, mature upper and lower surface center 84C, surrounding center 84B, margins 84A, fading to 72A and 72B in color, lower lip side lobes; 2, 5 mm in length, 0.5 mm in width, subulate in shape, acuminate apex, cuneate base fused to tube, inner and outer surface slightly translucent and densely pubescent with hairs up to 0.3 mm in length that match petal surface, color; inner and outer surface 75C, changing to 144B towards the tip with very tip 21A, upper lobes; 2-lobed, falcate in shape, margin entire, apex acute, 5 cm in length and 2 mm in width, base fused, upper and lower surface smooth, slightly glossy, base is densely pubescent with hairs on the upper and lower surface up to 1 mm in length, NN155A in color, color; young upper and lower surface 76C and 76D, margins faintly flushed with 76A, mature upper and lower surface center 84C, surrounding center 84B, margins 84A, tube; 8 mm in length and inner and outer surface very glossy and densely covered in pubescence up to 2.5 mm in length and NN155A in color, color; a blend of 76B, 76C and N77B also translucent at base becoming mostly 76D.

Reproductive organs:

*Gynoecium*.—Pistil; 1, 9 mm in length, style; 8 mm in length, 182B and 185A towards the top in color, stigma; cleft (2 parted), 1 mm in length and 185A in color, ovary; round and 145A in color.

*Androecium*.—Stamens; 4, filaments; base 145C changing to 182A in color, 1 cm in length, anthers; dorsifixed, narrow elliptic in shape, 1 mm in length, 0.3 mm in width, 179A in color, pollen; moderate in quantity and 167A in color.

*Fruit and seed*.—None have been observed to date.

It is claimed:

1. A new and distinct cultivar of *Teucrium* plant named 'Pride of Georgia' as herein illustrated and described.

* * * * *